(12) United States Patent
Furnish

(10) Patent No.: US 9,737,688 B2
(45) Date of Patent: Aug. 22, 2017

(54) MODULAR HANDLE ASSEMBLY FOR A STEERABLE CATHETER

(71) Applicant: Freudenberg Medical, LLC, Carpinteria, CA (US)

(72) Inventor: Greg Furnish, Louisville, KY (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 141 days.

(21) Appl. No.: 14/485,469

(22) Filed: Sep. 12, 2014

(65) Prior Publication Data

US 2016/0074625 A1    Mar. 17, 2016

(51) Int. Cl.
*A61M 25/01* (2006.01)

(52) U.S. Cl.
CPC .... *A61M 25/0147* (2013.01); *A61M 25/0136* (2013.01)

(58) Field of Classification Search
CPC .......... A61M 25/0133; A61M 25/0136; A61M 25/0147; A61M 2025/015; A61B 1/0052
See application file for complete search history.

(56) References Cited

U.S. PATENT DOCUMENTS

| | | | | |
|---|---|---|---|---|
| 5,364,351 A | * | 11/1994 | Heinzelman | ...... A61M 25/0147 600/585 |
| 6,522,933 B2 | | 2/2003 | Nguyen | |
| 2006/0100640 A1 | | 5/2006 | Bolduc | |
| 2013/0184642 A1 | | 7/2013 | O'Donnell et al. | |
| 2014/0135745 A1 | * | 5/2014 | Stenzel | ............ A61M 25/0127 606/1 |

FOREIGN PATENT DOCUMENTS

| | | |
|---|---|---|
| DE | 2752325 A1 | 7/1978 |
| EP | 1532999 A2 | 5/2005 |
| EP | 2438954 A1 | 4/2012 |
| WO | 2013190475 A2 | 12/2013 |
| WO | WO2014093457 A1 | 6/2014 |

OTHER PUBLICATIONS

European Search Report dated Jan. 29, 2016 in corresponding European Patent Application No. 15182404.2.

* cited by examiner

*Primary Examiner* — Laura Bouchelle
*Assistant Examiner* — Justin L Zamory
(74) *Attorney, Agent, or Firm* — Dickinson Wright PLLC

(57) ABSTRACT

A modular handle assembly for supporting and controlling a steerable catheter having at least one deflection wire includes a handle portion which extends along an axis for being secured about a portion of the steerable catheter. The modular handle assembly includes at least one barrel that is rotatably connected to the handle portion for rotation about said axis and at least one actuation screw shaft that is disposed within said handle portion and which extends through the barrel for connection with the deflection wire of the steerable catheter. At least one pinion gear is disposed radially between the actuation screw shaft and the barrel and is threadedly interconnected with the actuation screw shaft and the barrel for translating rotational movement of the barrel about the axis into axial movement of the actuation screw shaft to provide for movement of the deflection wire to curl the steerable catheter.

21 Claims, 4 Drawing Sheets

MODULAR HANDLE ASSEMBLY FOR A STEERABLE CATHETER

BACKGROUND OF THE INVENTION

1. Field of the Invention

The present invention relates to steerable catheters, and more particularly to a modular handle assembly for supporting and controlling a steerable catheter.

2. Description of the Prior Art

This section provides background information related to the present disclosure which is not necessarily prior art.

Catheters (i.e., catheters or sheaths) that have flexible tubular bodies with deflectable distal ends and control handles for controlling distal end deflection are used for many non-invasive medical producers. The distal portion of the catheter body is selectively deformed into a variety of curved configurations using an actuator on the control handle which remains outside the patient's body. The actuator is commonly internally linked to the distal portion of the catheter body by at least one deflection wire. Some catheter bodies employ a single deflection wire, which s pulled (i.e., placed in tension) by, the actuator in order to cause the distal portion of the catheter body to deform. Other catheter bodies having at least two deflection wires, where the displacement of one wire (i.e., placing one wire in tension) with the other wire going slack (i.e., the wire does carry a tensile load). In such catheters, where the deflection wires are not adapted to carry compressive loads (i.e., the deflection wires are only meant to be placed in tension), the deflection wires are commonly called pull or tension wires.

Although the prior art control handles are capable of controlling distal end deflection of catheter bodies, they have several drawbacks. For example, the prior art control handles are often excessively bulky and oftentimes expensive. Additionally, the prior art control handles often have a mechanical component that requires a significant effort to operate on the part of the user, and once a desired distal end deflection has been reached, the control handles typically require the operator to actuate a locking mechanism to maintain the catheter at the desired deflection. Further, the prior art control handles can not be easily modified, and thus are specifically designed to work with a specific steerable catheter design. Finally, the prior art control handles often subject the deflection wires to a tortuous path to steer a distal end of the catheter.

Accordingly, there remains a need in the art for an improved control handle for use with a steerable catheter.

SUMMARY OF THE DISCLOSURE

This section provides a general summary of the disclosure and is not intended to be a comprehensive disclosure of its full scope, aspects, objectives, and/or all of its features.

A modular handle assembly for supporting and controlling a steerable catheter includes a handle portion which extends along an axis for being secured about a portion of the steerable catheter. The module handle assembly includes at least one barrel rotatably connected to the handle portion for rotation about the axis and at least one actuation screw shaft disposed within the handle portion and extending through said barrel for connection with a deflection wire of the steerable catheter. The module handle assembly further includes at least one pinion gear disposed radially between the actuation screw shaft and the barrel and threadedly interconnecting the actuation screw shaft and said barrel for translating rotational movement of said barrel about the axis into axial movement of said actuation screw shaft to provide for movement of said deflection wire to curl the steerable catheter.

As will be described in more detail below, the subject modular handle assembly provides for equal or better steering performance of steerable catheters using less overall parts and a simpler design than the prior art handle assemblies. Accordingly, the subject modular handle assembly provides for a lower cost solution to steering a catheter. Additionally, the subject modular handle assembly is easily customizable to achieve two or four direction deflection of the distal end of the steerable catheter, and even customizable for use with a variety of different steerable catheter designs. Thus, the subject modular handle provides for increased flexibility and modularity over the prior art handle assemblies.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 2B is a magnified view of a first connector of FIG. 2 illustrating a plurality of passageways which extend axially therethrough;

DETAILED DESCRIPTION OF THE ENABLING EMBODIMENTS

Figure 1:
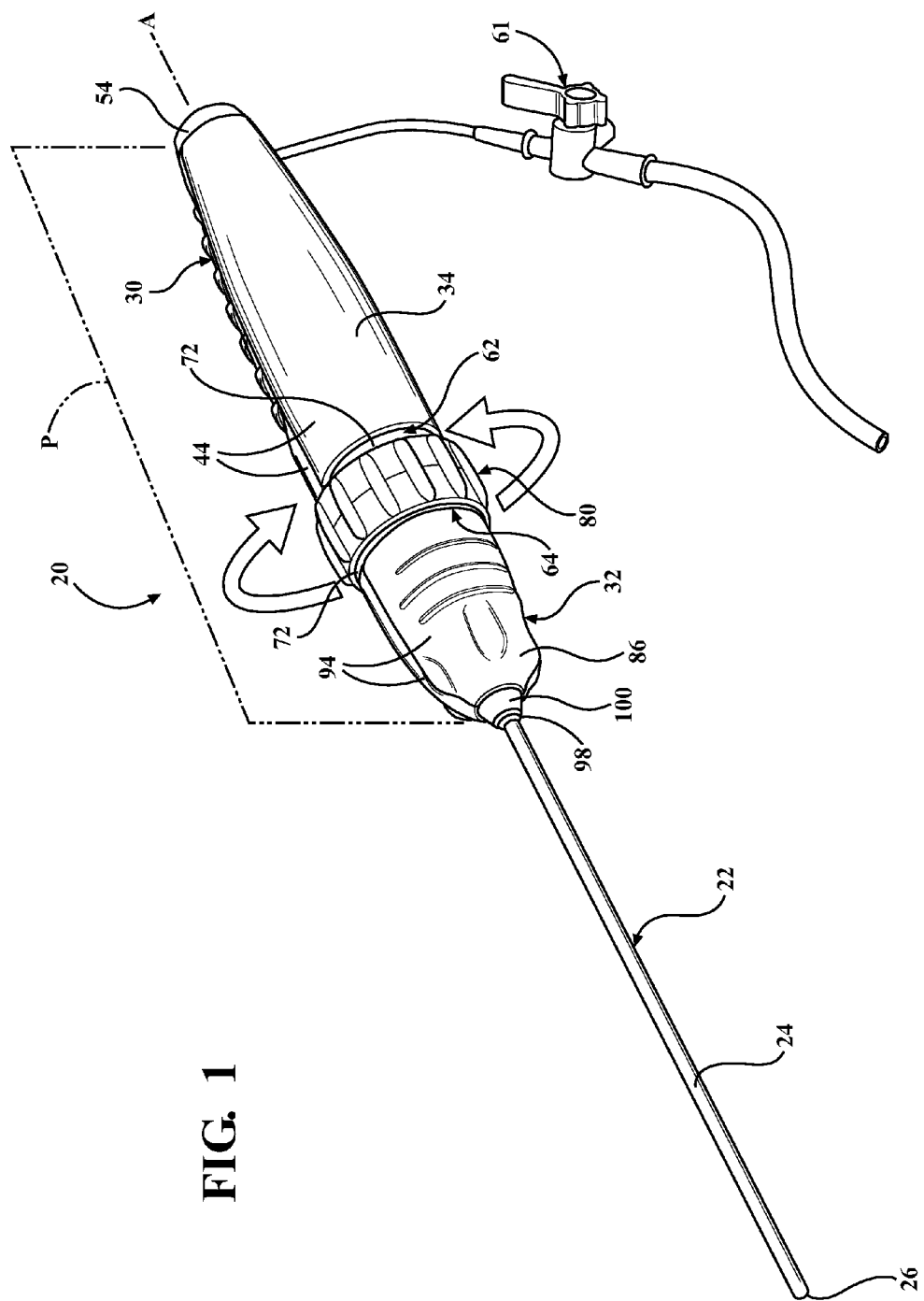
FIG. 1 is a perspective assembled view of a modular handle assembly constructed in accordance with the principles of the present disclosure.

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to a module handle assembly for supporting and controlling a steerable catheter.

Referring to the Figures, wherein like numerals indicate corresponding parts throughout the several views, a modular handle assembly 20, 120 for supporting and controlling a steerable catheter 22 that has a tubular, flexible elongated body 24 that extends to a distal tip 26. At least one deflection wire 28 extends from the distal tip 26 of the steerable catheter 22 and through the body 24 for curling the distal tip 26 in response to movement of the deflection wires 28.

The modular handle assembly 20, 120 includes a rear handle portion 30, generally indicated, that has a shell 34 and a skirt 36 for being disposed about and secured to the body 24 of the steerable catheter 22. The rear handle portion 30 has a hoop shaped cross-section that defines an inner wall 38 surrounding a hollow. However, the rear handle portion 30 could have other shapes including, but not limited to, a square shaped cross-section without departing from the scope of the subject disclosure. The rear handle portion 30 extends along an axis A from a first end 40 to a second end 42, and the shell 34 is tapered radially inwardly from the first end 40 to the skirt 36.

Figures 2, 2A:
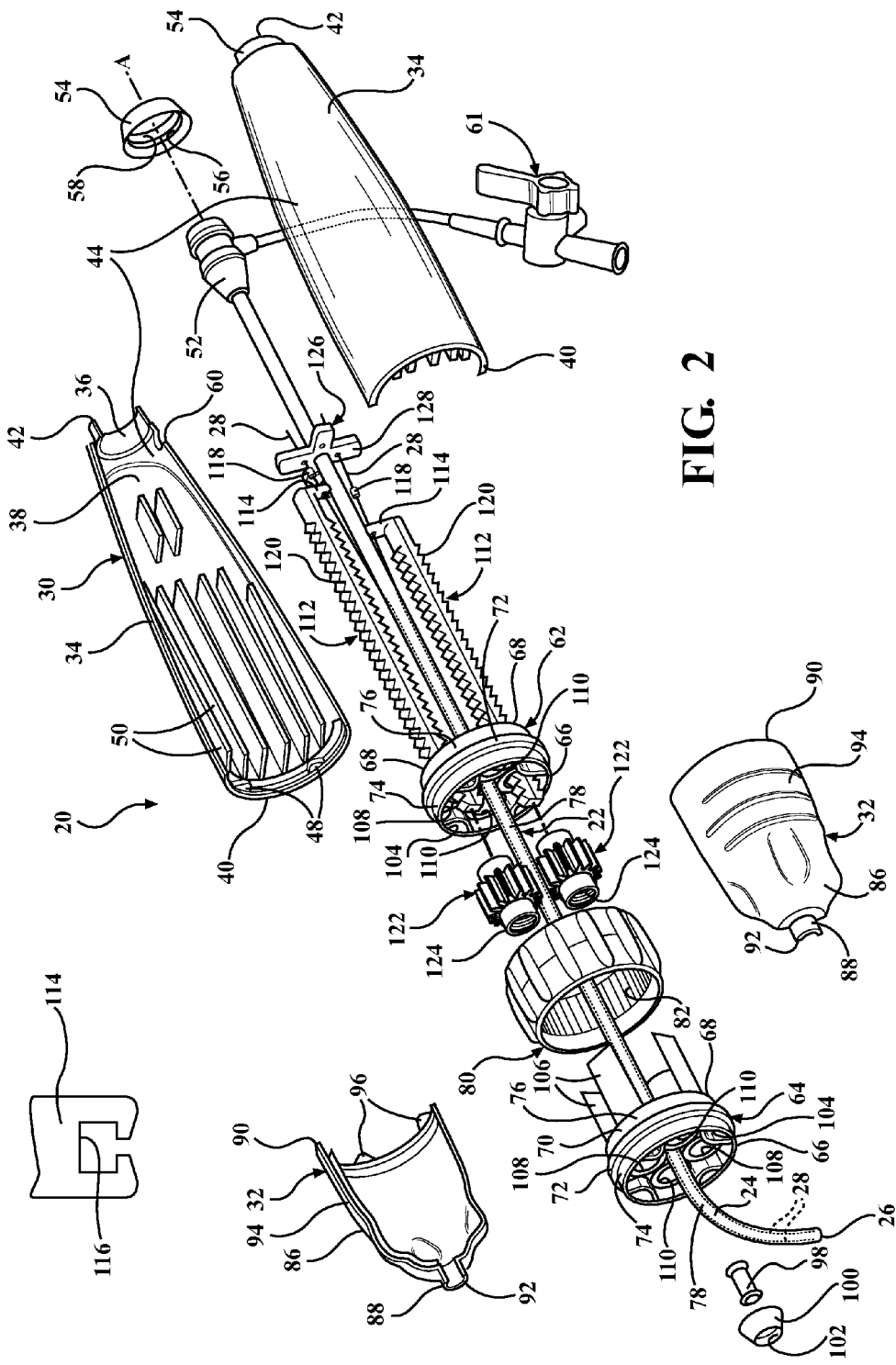
FIG. 2 is an exploded view of the assembled modular handle assembly illustrated in FIG. 1.
FIG. 2A is an magnified end view of a screw shaft of FIG. 2 illustrating a projection extending radially from the screw shaft and which defines a niche for receiving a deflection wire of a steerable catheter.
Figure 4:
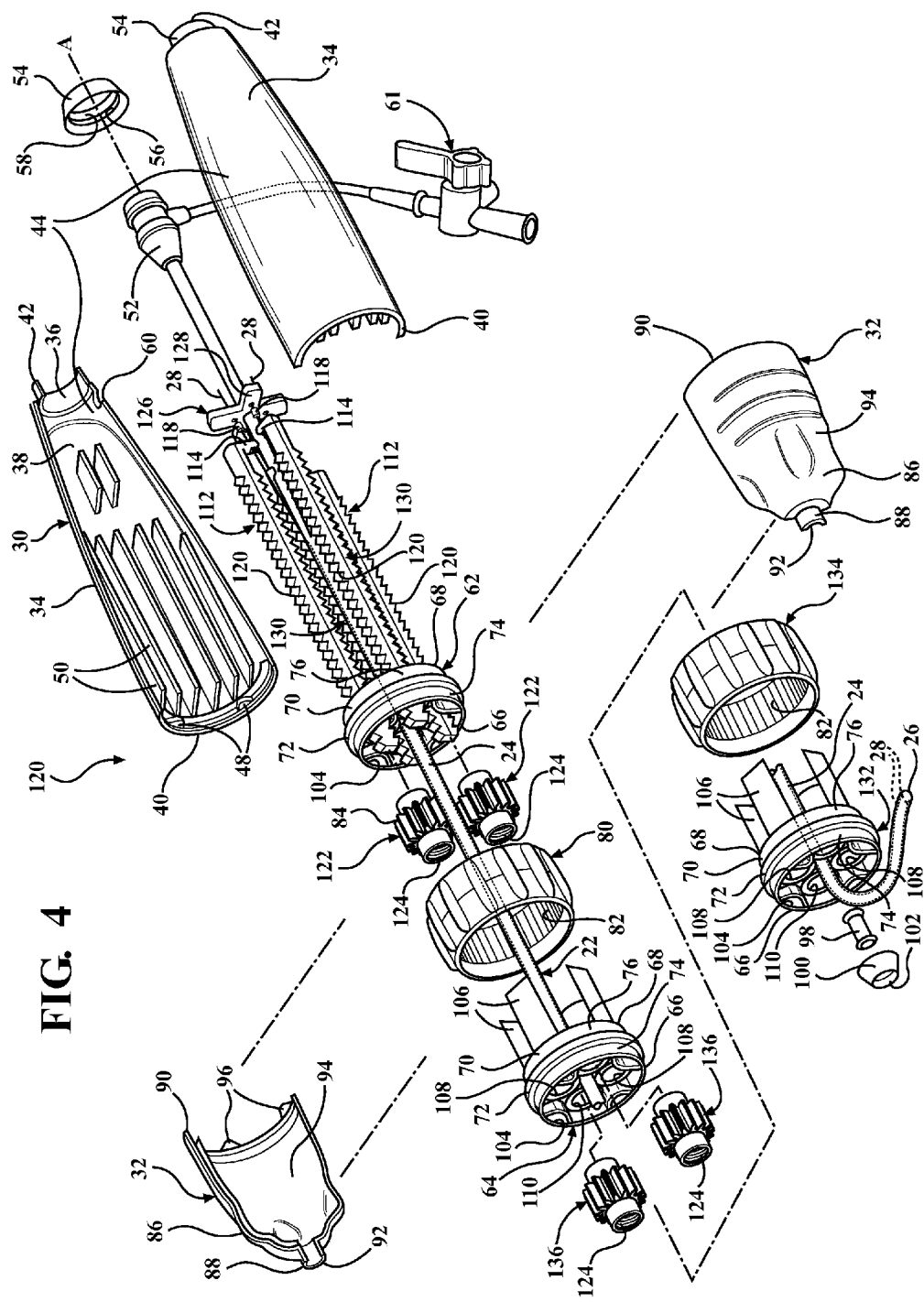
FIG. 4 is an exploded view of the assembled modular handle assembly illustrated in FIG. 4.

As best shown in FIGS. 2 and 4, the rear handle portion 30 further includes a pair of rear handle halves 44 that are mirror images with one another and which mate along a plane P that extends diametrically across the rear handle portion 30 through the axis A. A mechanical attachment 48, such as tabs, slots, nuts, bolts, or the like, removeably attaches the rear handle halves 44 to one another at the plane P. The construction of the modular handle assembly 20, 120 having two rear handle halves 44 advantageously provides for ease in manufacturing and assembly of the modular handle as the rear handle halves 44 can be molded separately. In addition, the two rear handle halves 44 provide for increased flexible modularity of the handle assembly as components internal to the rear handle portion 30 can easily be installed while the rear handle halves 44 are disconnected from one another.

A plurality of flanges 50 extend inwardly in spaced and parallel relationship with one another from the inner wall 38 of each of the rear handle halves 44 of the shell 34 for providing structural rigidity to the rear handle portion 30. It should be appreciated that any number of flanges 50 could be used to meet specific design needs and they could be oriented in other directions than shown in the Figures. The skirt 36 has a tube shape and extends at the second end 42 axially from the shell 34 for being disposed about and in engagement with a hero valve 52 for securing the catheter 22 to the rear handle portion 30. The skirt 36 also could be disposed about and in engagement with the body 24 of the steerable catheter 22.

A proximal cap 54 that has a generally hemispherical shape is disposed about the rear handle portion 30. The proximal cap 54 defines a recess 56 that has a cylindrical shape that extends axially therein. The recess 56 removeably receives the skirt 36 of the rear handle portion 30 to close the hollow of the rear handle portion 30 and to hold the rear handle halves 44 together in addition to the mechanical attachment 48. It should be appreciated that the recess 56 and skirt 36 could have cross-sections of other shapes including, but not limited to, a square shaped cross sections without departing from the scope of the subject disclosure. The proximal cap 54 further defines an opening 58 that extends therethrough along the axis A for surrounding the body 24 of the catheter. The shell 34 further defines arm orifice 60 that extends into the hollow adjacent to the skirt 36 at the plane 46 for receiving a hose of a stopcock assembly 61 of the steerable catheter 22.

As best shown in FIGS. 2 and 4, the modular handle assembly 20, 120 includes a first connector 62 and a second connector 64 each having a generally wheel shape and extending about the axis A. The first and second connectors 62, 64 each have a front face 66, a rear face 68, and an outside wall 70 that extends axially between the front face 66 and the rear face 68. A ring 72 extends radially outwardly from the outside wall 70 of each of the first and second connectors 62, 64 to axially divide each of the first and second connectors 62, 64 into a front segment 74 and a rear segment 76. The first end 40 of the shell 34 is disposed about and is connected to the rear segment 76 of the first connector 62 in axial abutment with the ring 72 of the first connector 62. The first and second connectors 62, 64 each further define a central passageway 78 that extends therethrough along the axis A for receiving the body 24 of the catheter. A first barrel 80 is disposed axially between the rings 72 of the first and second connectors 62, 64 and is rotatably disposed on the rear segment 76 of the second connector 64 and the front segment 74 of the first connector 62. The first barrel 80 has a generally tube shape to define an inside surface that presents a plurality of axially extending internal teeth 82. However, the internal teeth 82 could also extend in other directions without departing from the scope of the subject disclosure.

The modular handle assembly 20, 120 includes a front handle portion 32 that has a case 86 and a conduit 88 and a hoop shaped cross-section extends along the axis A from a first termination 90 to a second termination 92 for being disposed about the body 24 of the steerable catheter 22. The front handle portion 32 defines a chamber and includes a pair of front handle halves 94 that are mirror images with one another and mate along the plane 46. The front handle portion 32 also includes a mechanical coupling 96, such as tabs, slots, nuts, bolts, or the like, for removeably attaching the front handle halves 94 to one another at the plane 46. As best shown in FIGS. 1 and 2, in the first enabling embodiment, the second termination 92 of the case 86 is in axial abutment with the ring 72 of the second connector 64 about the front segment 74 of the second connector 64. Like the rear handle halves 44, it should be appreciated that the construction of the modular handle assembly 20, 120 having two front handle halves 94 advantageously provides for ease in manufacturing and assembly 20, 120 as the front handle halves 94 can be molded separately. In addition, the two front handle halves 94 provide for increased flexible modularity of the handle assembly as components internal to the rear handle portion 30 can easily be installed while the front handle halves 94 are disconnected from one another.

Figure 3:
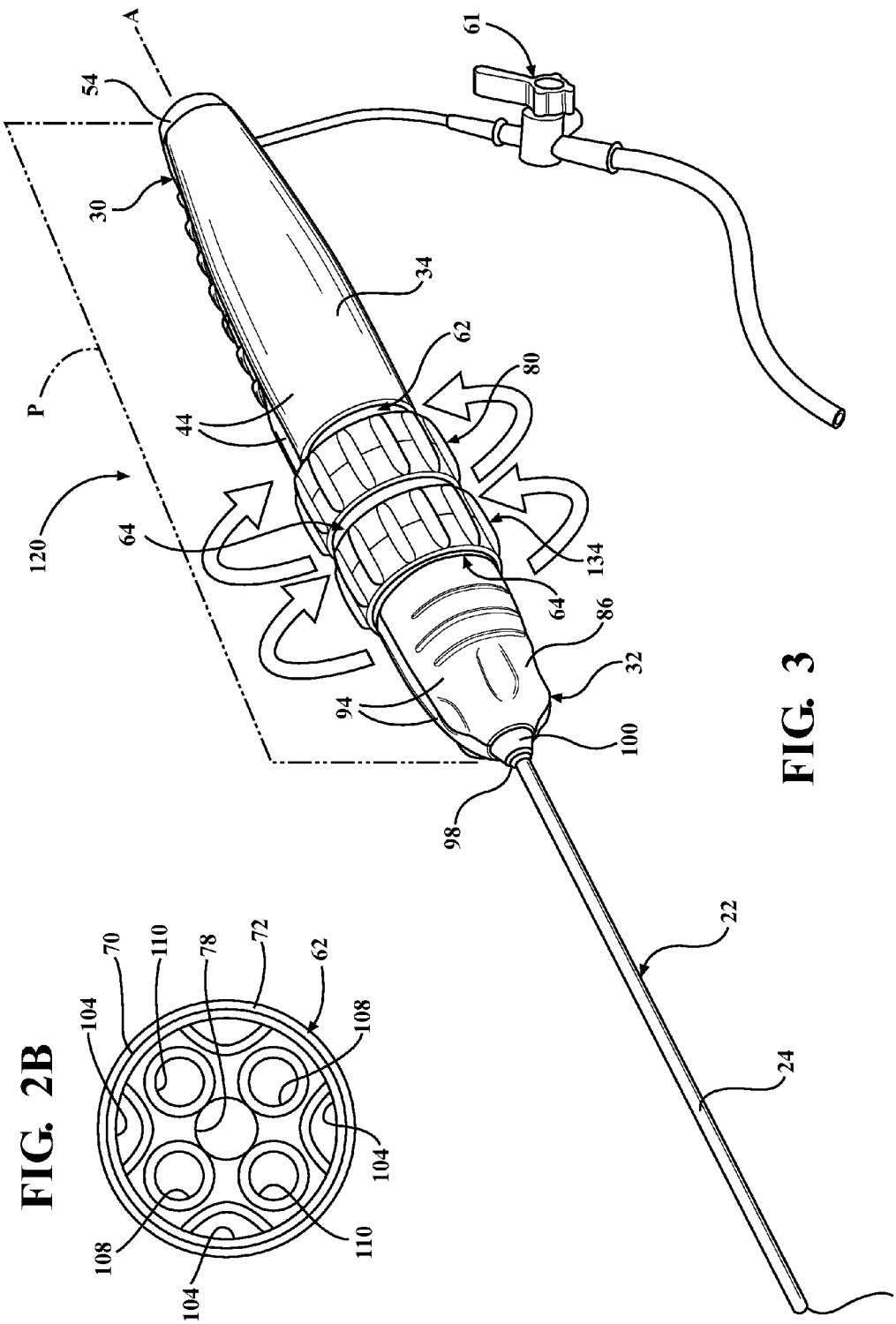
FIG. 3 is a perspective assembled view of a second embodiment of the modular handle assembly constructed in accordance with the principles of the present disclosure.

As best shown in FIGS. 1 and 3, the case 86 is tapered radially outwardly from the second termination 92 to the conduit 88, and the conduit 88 has a tube shape which extends at the first termination 90 axially from the case 86. A crimp pipe 98 that has a generally tube shape is disposed in the conduit 88 for being disposed about and in engagement with the body 24 of the catheter for tightening the front handle portion 32 about the body 24 of the steerable catheter 22. The crimp pipe 98 has a thickness that can vary based on the diameter of the body 24 of the steerable catheter 22 to ensure that the front handle portion 32 is tightened about the body 24 of the steerable catheter 22. Put another way, the size of the crimp tube 98 can be adjusted to accommodate a wired range of differently sized catheters 22, and thus provides for improved modularity of the subject handle assembly 20. It should be appreciated that the crimp pipe 98 could extend axially to other lengths, such as to the central passageway 78 of the first connector 62 to advantageously hold the body 24 of the steerable catheter 22 in place along a further length. It also should further be appreciated that the elongated body 24 of the steerable catheter 22 can be secured to the modular housing assembly 20 at various points along the length of the modular housing assembly 20 advantageously preventing the elongated body 24 of the catheter from twisting or binding up within the modular housing assembly 20 as is known to be a common issue in prior art handle assemblies 20.

As further shown in FIGS. 1 and 3, the modular handle assembly 20, 120 includes a distal cap 100 that has a generally hemispherical shape and is disposed about the front handle portion 32. The distal cap 100 defines a passage 102 that extends axially therethrough to removeably receive the conduit 88 of the front handle portion 32 and to hold the from handle halves 94 in addition to the mechanical coupling 96. It should be appreciated that an additional crimp pipe 98 could be disposed in the conduit 88 for being positioned about the body 24 of the steerable catheter 22 to ensure that the front handle portion 32 is tightened about the body 24. Similar to the crimp tube 98, the passage 102 of the distal cap 100 can be adjusted to accommodate a wide range of differently sized catheters 22, and thus provide for improved modularity of the subject handle assembly 20.

As best shown in FIGS. 2 and 4, the front face 66 of each of the first and second connectors 62, 64 defines four channels 104 that extend therein and which are circumferentially and evenly spaced about the central passageway 78. The second connector 64 additionally includes four legs 106 that extend axially from the rear face 68 of the second connector 64 and are circumferentially and evenly spaced from one another about the central passageway 78. Each of the four legs 106 are each received by one of the channels 104 of the first connector 62 for connecting the first and second connectors 62, 64 in axially spaced relationship with one another. It should be appreciated that alternatively, any other number of channels 104 and corresponding legs 106 could be present on the first and second connectors 62, 64 based on design needs. As further shown in FIGS. 2 and 4, the first and second connectors 62, 64 also define a pair of horizontal outer passageways 108 that extend axially therethrough and which are aligned with one another on opposing sides of the axis A. Additionally, the first and second connectors 62, 64 define a pair of vertical outer passageways 110 that extend axially therethrough and which are aligned with one another on opposing sides of the axis A and circumferentially disposed between the horizontal outer passageways 108.

A pair of horizontal actuation screw shafts 112 each extend through one of the horizontal outer passageways 108 of the first and second connector 62, 64 and into the hollow of the rear handle portion 30. Each of the horizontal actuation screw shafts 112 includes a projection 114 that extends radially toward the axis A from each of the horizontal actuation screw shafts 112 for connection with one of the deflection wires 28. As best presented in FIG. 2A, each of the projections 114 defines a niche 116 that has a T-shape extending therein for receiving one of the deflection wires 28. The T-shape of the niche 116 advantageously allows the deflection wire 28 to easily be threaded into the niche, and thus improves the assembly and modularity of the subject handle assembly 20. The deflection wires 28 are held in place by the niche 116 in conjunction with the tension of the deflection wire 28 within the niche 116. The niche 116 can also be designed with different shapes, such as L-shaped, without departing from the scope of the subject disclosure. A wire crimp 118 is fixedly disposed about each of the deflection wires 28 axially past the niche 116 of the horizontal actuation screw shafts 112 and next adjacent the distal cap 100 for preventing the deflection wire 28 from axially sliding out of the niche 116 during axial movement of the horizontal actuation screw shafts 112. The wire crimp 118 advantageously allows the deflection wires 28 to slide axially back and forth through their respective niches 116 to a predetermined extent during axial movement of the screw shafts 112, but will not allow the deflection wires 28 to slide out of the niche 116. As a result, the design of the niche 116 prevents the build-up of slack of the deflection wires 28 within the hollow of the rear handle 30. Put another way, the niche 116 allows for sliding of the deflection wire through the niche 116 when the actuation screws are moving in a distal axial direction, and the crimp 118 facilitates a pulling of the deflection wire when the actuation screws are moving in a proximal axial direction. As a result, the niche 116 and crimp 118 effectuate a tension-only action on the deflection wires 28.

As best shown in FIGS. 2 and 4, each of the horizontal actuation screw shafts 112 has an outer surface that presents a plurality of external threads 120. A rear pinion gear 122 is disposed about and axially aligned with each one of the horizontal actuation screw shafts 112, and disposed axially between the first and second connectors 62, 64. The rear pinion gear 12 has a generally tube shape to define an internal and external surface. The external surface of the rear pinion gears 122 presents a plurality of axially extending external teeth 84 for mating with the internal teeth 82 of the first barrel 80 for providing for rotational movement of the rear pinion gears 122 in response to rotation of the first barrel 80. The external teeth 84 could extend in other directions but they should mate with the internal teeth 82 of the first barrel 80. The internal surface of each of the rear pinion gears 122 presents a plurality of internal threads 124 that are threadedly connected with the external threads 120 of the horizontal actuation screw shaft 112. An arrangement in this regard provides for axial movement of the horizontal actuation screw shaft 112 relative to the rear pinion gear 122 in response to rotation of the rear pinion gear 122 about the horizontal actuation screw shaft 112 as a result of the first barrel 80 being rotated about the axis A. Accordingly, the pinion gears 122 translate rotational movement of the first barrel 80 about the axis A into axial movement of the horizontal actuation screw shaft 112 to provide for movement of the deflection wire 28 to curl the distal tip 26 the steerable catheter 22 horizontally.

In one embodiment, the external threads 120 of each of the horizontal actuation screw shafts 112 extend in opposing directions with one another for providing for axial movement of the horizontal actuation screw shafts 112 in opposite axial directions from one another. Movement in this regard moves the deflection wires 28 in opposite directions from one another to allow the steerable catheter 22 to be curled in two horizontal or directly opposing directions. However, in another embodiment, the external threads 120 of each of the horizontal actuation screw shafts 112 could extend in the same direction with one another for providing for axial movement of the horizontal actuation screw shafts in the same axial direction. The external threads 120 of the horizontal actuation screw shafts 112 and the internal threads 124 of the pinion gears 122 could also be oriented at various pitches to provide for increased or decreased axial movement of the horizontal actuation screw and deflection wire 28 per revolution of the first barrel 80 based on design needs. The interchangeability of the external threads 120 of the horizontal actuation screw shafts 122 provides for increased modularity for the subject handle assembly 20.

Thus, as can be understood from the aforementioned disclosure in connection with the Figures, when the external threads 120 of each of the horizontal actuation screw shafts 112 extend in opposing directions with one another, as the first barrel 80 is rotated clockwise relative to the axis A, the internal teeth 82 of the first barrel 80 being meshed with the external teeth 84 of the pinion gears 122, in conjunction with the internal threads 124 of the pinion gears 122 being threaded with the external threads 120 of the actuation screw shafts 112 cause simultaneous opposed displacement of the horizontal actuation screw shafts 112 longitudinally or axially within the handle assembly 20. Specifically, because of the meshed and threaded relationship of the first barrel 80, the pinion gears 122, and the screw shafts 112, one of the horizontal actuation screw shafts 112 moves distally within the handle assembly 20 and the other of the horizontal actuation screw shafts 112 moves proximally within the handle assembly 20 when the first barrel 80 is rotated clockwise to relative to the rear handle portion 30 and the front handle portion 32. Conversely, when the first barrel 80 is rotated in a counterclockwise manner relative to the rear handle portion 30 and the front handle portion 32, each of the horizontal actuation screw shafts 112 reverse or alternate their axial direction.

With reference to FIGS. 2 and 4, when the first barrel 80 is rotated such that the first one of the horizontal actuation screw shafts 112 is urged distally and the other one of the horizontal actuation screw shafts 112 is urged proximally, the distal end 26 of the catheter body 24 is caused to deflect in a first direction. Conversely, when the first barrel 80 is rotated such that the directions of the horizontal actuation screw shafts 112 is reversed, the distal end 26 of the catheter body 24 to deflect in a second direction that is directly opposite to the first direction. Although the actuation screw shafts are described throughout the specification as being horizontal, it should be appreciated that movement of the horizontal actuation screw shafts 112 need not result in horizontal deflection of the catheter 24, but rather just two movements of the distal end 26 of the catheter body 24 which occur directly opposite to one another. Accordingly, the horizontal actuation screw shafts 112 of the first embodiment the modular handle assembly 20 provide for two (2) direction deflection of the distal end 26 of the catheter body 24.

Additionally, the meshed and threaded relationship of the first barrel 80, the pinion gears 122, and the screw shafts 112, provides for a natural means to lock the deflection of the distal end 26 of the catheter body 24 without the need for an additional lock control mechanism as is required in the prior art handle assemblies. Put another way, an operator or user of the modular handle assembly 20 can simply hold the first barrel 80 in place, which prevents the distal end 26 of the catheter body 24 from moving because of the intermeshed and threaded relationship of the first barrel 80, the pinion gears 122, and the screw shafts 112.

As best shown in FIGS. 2 and 4, a stop 126 is disposed in the hollow of the rear handle portion 30 axially adjacent to the skirt 36 for limiting axial movement of the horizontal actuation screw shafts 112. In a preferred arrangement, the stop 126 has a cross shape to define a center and four arms 128 that extend radially outwardly from the center. Two of the arms 128 are each in axial alignment with one of the horizontal actuation screw shafts 112 for limiting the axial movement of the horizontal actuation screw shafts 112. This advantageously prevents the horizontal actuation screw shafts 112 from axially moving out of the pinion gears 122. As will be described in more detail below, the other arms 128 of the stop 126 could be used to limit axial movement of additional actuation screw shafts 112, 130. However, the modular handle assembly 20 could omit the stop 126 without departing from the scope of the subject disclosure.

In a second enabling embodiment, the modular handle assembly 20 includes a third connector 132 which a generally wheel shape and which extends about the axis A. As best shown in FIG. 4, like the first and second connectors 62, 64, the third connector 132 has a front face 66 and a rear face 68 and has an outside wall 70 that extends axially between the front face 66 and the rear face 68. A ring 72 extends radially outwardly from the outside wall 70 of the third connector 132 to axially divide the third connector 132 into a front segment 74 and a rear segment 76. The third connector 132 further defines a central passageway 78 that extends therethrough along the axis A for receiving the body 24 of the steerable catheter 22.

As best shown in FIGS. 3 and 4, the second enabling embodiment of the modular handle assembly 20 includes a second barrel 134 that is rotatably disposed on the rear segment 76 of the third connector 132 and the front segment 74 of the second connector 64 and axially between the rings 72 of the second and third connectors 64, 132. Like the first barrel 80, the second barrel 134 has a generally tubular shape to define an inside surface that presents a plurality of axially extending internal teeth 82. The front face 66 of the third connector 132 further defines four channels 104 that extend axially therein and which are circumferentially and evenly spaced about the central passageway 78. The third connector 132 further includes four legs 106 that extend axially from the rear face 68 of the third connector 132 and which are circumferentially and evenly spaced from one another about the central passageway 78. Each of the legs 106 are received by one of the channels 104 of the second connector 64 for connecting the second and third connectors 64, 132 in axially spaced relationship with one another. It should be appreciated that alternatively any other number of channels 104 and corresponding legs 106 could be present on the second and third connectors 64, 132 based on design needs.

The third connector 132 further defines a pair of horizontal outer passageways 108 that extend therethrough in parallel and aligned relationship with the axis A and which are aligned with one another on opposing sides of the axis A. The third connector 132 also defines a pair of vertical outer passageways 110 that extend therethrough in parallel and aligned relationship with the axis A and which are aligned with one another on opposing sides of the axis A and circumferentially spaced between the horizontal outer passageways 108. The pair of horizontal actuation screw shafts 112 each further extend through one of the horizontal outer passageways 108 of the third connector 132. A pair of vertical actuation screw shafts 130 each extend through one of the vertical outer passageways 110 of the first, second and third connectors 62, 64, 132 and into the hollow of the rear handle portion 30. Like the horizontal actuation screw shafts 112, each of the vertical actuation screw shafts 130 includes a projection 114 that extends radially toward the axis A from each of the vertical actuation screw shafts 130 each for connecting with one of additional deflection wires 28. Additional wire crimps 118 are fixedly disposed about each of the additional deflection wires 28 axially past the niche 116 of the vertical actuation screw shafts 130 and next adjacent toward the distal cap 100 for preventing the deflection wires 28 from axially sliding out of the niche 116 during axial movement of the vertical actuation screw shafts 130. The wire crimp 118 advantageously allows the deflection wires 28 to slide axially back and forth through their respective niches 116 to a predetermined extent during axial movement of the vertical actuation screw shafts 130, but will not allow the deflection wires 28 to slide out of the niche 116. As a result, the design of the niche 116 prevents the build-up of slack of the deflection wires 28 within the hollow of the rear handle 30.

Each of the vertical actuation screw shafts 130 have an outer surface that presents external threads 120, with the external threads 120 of each of the vertical actuation screw shafts 130 extending in an opposing direction relative to the other. A front pinion gear 136 is disposed about each of the vertical actuation screw shafts 130 and axially between second and third connectors 64, 132. Like the rear pinion gears 122, each of the front pinion gears 136 has a generally tube shape to define an internal surface and an external surface, with the external surface of the front pinion gears 136 presenting a plurality of external teeth 84 for mating with the internal teeth 82 of the second barrel 134 for providing for rotational movement of the front pinion gears 136 in response to rotation of the second barrel 134. The internal surface of each of the from pinion gears 136 presents internal threads 124 threadedly connected with the external threads 120 of the vertical actuation screw shall 130. An arrangement in this regard provides for axial movement of the vertical actuation screw shaft 130 relative to the front pinion gear 136 in response to rotation of the from pinion gear 136 about the vertical actuation screw shaft 130 as a result of second barrel 134 being rotated about the axis A. Accordingly, the front pinion gears 136 provide for movement of the deflection wires 28 to curl the distal tip 26 of the elongated body 24 vertically or transversely relative to the movement effectuated by the horizontal actuation screw shafts 112. Put another way, the front pinion gears 136 translate rotational movement of the second barrel 134 about the axis A into axial movement of the vertical actuation screw shaft 130 to provide for movement of the deflection wire 28 to curl the distal tip 26 of the steerable catheter 22 in a direction which is transverse to the movement of the distal tip 26 effectuated by the horizontal actuation screw shafts 112.

The external threads 120 of each of the vertical actuation screw shafts 130 extend in opposing directions with one another for providing for axial movement of the vertical actuation screw shafts 130 in opposite axial directions. Movement in this regard moves the deflection wires 28 in opposite directions from one another to allow the steerable catheter 22 to be curled in two vertical or directly opposing directions. However, in another embodiment, the external threads 120 of each of the vertical actuation screw shafts 130 could extend in the same direction with one another for providing for axial movement of the vertical actuation screw shafts 130 in the same axial direction. Like the horizontal actuation screw shafts 112, the external threads 120 of the vertical actuation screw shafts 130 could advantageously be oriented at various pitches to provide for increased or decreased axial movement of the vertical actuation screw shaft 130 and corresponding deflection wire 28 per revolution of the second barrel 134 based on design needs. The interchangeability of the external threads 120 of the horizontal actuation screw shafts 122 provides for increased modularity for the subject handle assembly 20. As mentioned above, the other arms 128 of the stop 126 each are in axial alignment with one of the vertical actuation screw shafts 130 for limiting the axial movement of the vertical actuation screw shafts 130.

Thus, as can be understood from the aforementioned disclosure in connection with the Figures, as the second barrel 134 is rotated clockwise relative to the axis A, the internal teeth 82 of the second barrel 134 being meshed with the external teeth 84 of the front pinion gears 136, in conjunction with the internal threads 124 of the front pinion gears 136 being threaded with the external threads 120 of the vertical actuation screw shafts 130 cause simultaneous opposed displacement of the vertical actuation screw shafts 130 longitudinally or axially within the handle assembly 20 when the external threads 120 extend in opposing directions. Specifically, because of the meshed and threaded relationship of the second barrel 134, the front pinion gears 136, and the vertical screw shafts 130, one of the vertical actuation screw shafts 130 moves distally within the handle assembly 20 and the other of the vertical actuation screw shafts 130 moves proximally within the handle assembly 20 when the second barrel 134 is rotated clockwise to relative to the rear handle portion 30 and the front handle portion 32. Conversely, when the second barrel 134 is rotated in a counterclockwise manner relative to the rear handle portion 30 and the front handle portion 32, each of the vertical actuation screw shafts 134 reverse or alternate their axial direction.

With reference to FIG. 4, when the second barrel 134 is rotated such that the first one of the vertical actuation screw shafts 130 is urged distally and the other one of the vertical actuation screw shafts 130 is urged proximally, the distal end 26 of the catheter body 24 deflects in a second direction which is transverse to the direction effectuated by the horizontal actuation screw shafts 112. Conversely, when the second barrel 134 is rotated such that the directions of the vertical actuation screw shafts 130 are reversed, the distal end 26 of the catheter body 24 deflects in the opposite direction. Although the actuation screw shafts are described throughout the specification as being vertical, it should be appreciated that movement of the vertical actuation screw shafts 130 need not result in vertical deflection of the catheter 24, but rather just movement of the distal end 26 of the catheter body 24 which occurs transverse to the movement effectuated by the horizontal actuation screw shafts 112. Thus, the second embodiment of the modular handle assembly 20 provides for four (4) direction deflection of the distal end 26 of the catheter body 24. In addition, as can be understood from the aforementioned disclosure, the subject handle assembly 20 can be easily modified to incorporate the second barrel 134, the front pinion gears 136, and the vertical actuation screw shafts 130 to provide the four (4) direction deflection, and thus provides for more flexibility and modularity over the prior art handle assemblies. Further, the subject modular handle assembly 20 achieves the four (4) direction deflection of the distal end 26 of the catheter body 24 using less overall parts and a simpler design than the prior art handle assemblies.

Due to the modular construction of modular handle assembly 20, additional barrels 134, 80, pinion gears 122, connectors 132, 62, 64 and screw shafts 112, 130 could be added to the assembly 20 in the same fashion as the second enabling embodiment to provide for movement of the steerable catheter 22 in a wide variety other directions or along different lengths along the body 24 of the steerable catheter 22.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular handle assembly for supporting and controlling a steerable catheter having at least one deflection wire, said modular handle assembly comprising;
   a handle portion extending along an axis for being secured about a portion of the steerable catheter,
   at least one barrel rotatably connected to said handle portion for rotation about said axis, said at least one barrel having an inside surface presenting a plurality of internal teeth,
   at least one actuation screw shaft disposed within said handle portion and extending through said at least one barrel for connection with the at least one deflection wire of the steerable catheter, said at least one actuation screw shaft having an outer surface presenting a plurality of external threads,
   at least one pinion gear threadedly interconnecting said at least one actuation screw shaft and said at least one barrel,
   said at least one pinion gear having an external surface presenting a plurality of external teeth mating with said internal teeth of said barrel for providing rotational movement of said at least one pinion gear in response to said rotation of said at least one barrel about said axis, and
   said at least one pinion gear having an internal surface presenting a plurality of internal threads being threadedly connected with said external threads of said at least one actuation screw shaft for translating rotational movement of said at least one barrel about said axis into axial movement of the at least one actuation screw shaft to provide for movement of said at least one deflection wire to curl the steerable catheter.

2. The modular handle assembly as set forth in claim 1, wherein said at least one actuation screw shaft includes a pair of horizontal actuation screw shafts disposed in spaced and parallel relationship with one another for each being connected with a respective deflection wire, and said at least one pinion gear includes a pair of pinion gears each disposed radially between one of said horizontal actuation screw shafts and said at least one barrel and threadedly interconnecting said respective one of said horizontal actuation screw shafts and said at least one barrel.

3. The modular handle assembly as set forth in claim 2 wherein said external threads of each of said horizontal actuation screw shafts extend in opposing directions with one another to provide for axial movement of said horizontal actuation screws in opposite axial directions.

4. The modular handle assembly as set forth in claim 2, wherein said external threads of each of said horizontal actuation screw shafts extend in the same direction with one another to provide for axial movement of said horizontal actuation screws in the same axial direction.

5. The modular handle assembly as set forth in claim 2, wherein said external threads of each of said horizontal actuation screw shafts are oriented at different pitches relative to one another to provide for different rates of axial movement of said horizontal actuation screw shafts relative to one another per revolution of said at least one barrel.

6. The modular handle assembly as set forth in claim 1, further comprising:
   wherein said at least one actuation screw shaft includes a pair of horizontal actuation screw shafts and a pair of vertical actuation screw shafts disposed in spaced and parallel relationship with one another for each being connected with a respective deflection wire,
   said at least one pinion gear includes a pair of rear pinion gears and a pair of front pinion gears,
   said at least one barrel includes a first barrel and a second barrel axially spaced from one another,
   said rear pinion gears are each disposed radially between one of said horizontal actuation screw shafts and said first barrel and threadedly interconnecting said horizontal actuation screw shafts and said first barrel, and
   said front pinion gears each disposed radially between one of said vertical actuation screw shafts and said second barrel and threadedly interconnecting said vertical actuation screw shafts and said second barrel.

7. The modular handle assembly as set forth in claim 6 wherein said external threads of each of said horizontal actuation screw shafts extend in opposing directions with one another for providing for axial movement of said horizontal actuation screws in opposite axial directions to move said deflection wires in opposite directions from one another to allow the steerable catheter to be curled in two opposing horizontal directions, and said external threads of each of said vertical actuation screw shafts extend in opposing directions with one another for providing for axial movement of said vertical actuation screws in opposite axial directions to move said deflection wires in opposite directions from one another to allow the steerable catheter to be curled in two opposing vertical directions.

8. The modular handle assembly as set forth in claim 1, further comprising a first connector and a second connector each having a generally wheel shape and extending about said axis and each having a front face and a rear face and each having an outside wall extending axially between said front face and said rear face.

9. The modular handle assembly as set forth in claim 8, further comprising a ring extending radially outwardly from said outside wall of each of said first and second connectors to axially divide each of said first and second connectors into a front segment and a rear segment.

10. The modular handle assembly as set forth in claim 9, wherein said at least one barrel is axially disposed between said rings of said first and second connectors and rotatably disposed on said rear segment of said second connector and said front segment of said first connector.

11. The modular handle assembly as set forth in claim 10, wherein said first and second connectors each define a central passageway extending therethrough along said axis for receiving the steerable catheter.

12. The modular handle assembly as set forth in claim 11, wherein said front face of each of said first and second connectors defines at least one channel extending therein spaced from said central passageway.

13. The modular handle assembly as set forth in claim 12, wherein said second connector includes at least one leg being received by said channel of said first connector connecting said first and second connectors in axially spaced relationship with one another.

14. The modular handle assembly as set forth in claim 13, wherein said first and second connectors each define at least one outer passageway extending therethrough.

15. The modular handle assembly as set forth in claim 14, wherein said at least one actuation screw shaft extends through said outer passageways of said first and second connectors.

16. The modular handle assembly as set forth in claim 1, wherein said at least one actuation screw shaft includes a projection extending radially toward said axis for connecting with the at least one deflection wire.

17. The modular handle assembly as set forth in claim 16, wherein said projection defines a niche having a T-shape extending therein for removably receiving the at least one deflection wire to connect the at least one deflection wire with said at least one actuation screw shaft and for allowing the at least one deflection wire to slide within said niche during axial distal movement of said at least one actuation screw shaft.

18. The modular handle assembly as set forth in claim 17, further comprising a wire crimp fixedly disposed about the at least one deflection wire axially proximal of said niche of said at least one actuation screw shaft for preventing the at least one deflection wire from axially sliding out of said niche during axial proximal movement of said at least one actuation screw shaft.

19. A modular handle assembly for supporting and controlling a steerable catheter having at least one deflection wire, said modular handle assembly comprising,
   a handle portion extending along an axis for being secured about a portion of the steerable catheter,
   at least one barrel rotatably connected to said handle portion for rotation about said axis,
   at least one actuation screw shaft disposed within said handle portion and extending through said at least one barrel for connection with the at least one deflection wire of the steerable catheter,
   at least one pinion gear threadedly interconnecting said at least one actuation screw shaft and said at least one barrel for translating rotational movement of said at least one barrel about said axis into axial movement of said at least one actuation screw shaft to provide for movement of the at least one deflection wire to curl the steerable catheter,
   a first connector and a second connector each having a generally wheel shape and extending about said axis and each having a front face and a rear face and each having an outside wall extending axially between said front face and said rear face,
   a ring extending radially outwardly from said outside wall of each of said first and second connectors to axially divide each of said first and second connectors into a front and rear segment,
   said at least one barrel axially disposed between said rings of said first and second connectors and rotatably disposed on said rear segment of said second connector and said front segment of said first connector,
   each of said first and second connectors defining a central passageway extending therethrough along said axis for receiving the steerable catheter,
   said front face of each of said first and second connectors defining at least one channel extending therein spaced from said central passageway, and
   said second connector including at least one leg received by said channel of said first connector and connecting said first and second connectors in axially spaced relationship with one another.

20. The modular assembly as set forth in claim 19, wherein said first and second connectors each define at least one outer passageway extending therethrough.

21. The modular assembly as set forth in claim 20, wherein said at least one actuation screw shaft extends through said outer passageways of said first and second connectors.

* * * * *